United States Patent [19]

Wei

[11] 4,289,697

[45] Sep. 15, 1981

[54] 5-SUBSTITUTED 4-HYDROXY-2,3-ALKYLENE THIAZOLIUM SALTS

[75] Inventor: Peter H. L. Wei, Springfield, Pa.

[73] Assignee: American Home Products Corporation, New York, N.Y.

[21] Appl. No.: 197,359

[22] Filed: Oct. 15, 1980

[51] Int. Cl.³ .......................................... C07D 513/04
[52] U.S. Cl. ................................. 260/245.5; 546/114
[58] Field of Search ...................... 546/114; 260/245.5

[56] References Cited

U.S. PATENT DOCUMENTS 4,246,266   1/1981   Undheim et al. .................. 546/114

*Primary Examiner*—Henry R. Jiles
*Assistant Examiner*—Bernard Dentz
*Attorney, Agent, or Firm*—Richard K. Jackson

[57] ABSTRACT

Substituted 4-hydroxy-2,3-alkylene thiazolium salts are anti-secretory agents useful in the treatment of peptic ulcer disease.

4 Claims, No Drawings

5-SUBSTITUTED 4-HYDROXY-2,3-ALKYLENE THIAZOLIUM SALTS

DESCRIPTION OF THE INVENTION

In accordance with this invention there is provided a group of anti-secretory compounds, useful in the treatment of peptic ulcer disease, of the formula:

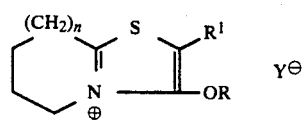

in which
R$^1$ is phenyl, halophenyl, alkylphenyl of 7 to 10 carbon atoms, nitrophenyl or aminophenyl;
R$^2$ is hydrogen or alkanoyl of 2 to 4 carbon atoms;
Y is the anion of a pharmaceutically acceptable acid; and
n is one of the integers 1 or 2.

The pharmaceutically acceptable acids providing the anion Y may be of organic or inorganic origin, such as hydrochloric, hydrobromic, hydroiodic, sulfuric, phosphoric, nitric, formic, acetic, trifluoroacetic, propionic, succinic, lactic, malic, citric, maleic, benzoic, salicylic, methanesulfonic, acid and the like. The halo substituent of the halophenyl group may be chlorine, bromine, fluorine or iodine.

The anti-ulcer agents of this invention function in their anti-secretory capacity to reduce (1) total gastric volume, (2) hydrogen ion secretion, or (3) hydrogen ion concentration. The reduction of any one of these parameters aids in attenuating the general debilitating influence of a peptic ulcer.

Each of the compounds depicted were found active in the following scientifically recognized, standard test for anti-secretory activity:

Male Charles River rats weighing 190-260 grams are deprived of food but not water for 18 hours prior to use. Water is, however, withheld during the experiment. The rats are weighed, anesthetized with ether and the pylorus ligated according to the method of Shay et al., Gastroenterology 26: 906-913 (1954). Treatment or vehicle control is then administered interduodenally (i.d.). Rats are housed two per cage and sacrificed with CO$_2$ four hours after ligation. The stomachs are removed, rinsed, and contents emptied into a graduated centrifuge tube. The tubes are centrifuged for 20 minutes at 2,000 RPM and the volume of gastric juice recorded. Any samples obviously contaminated by feces, food or blood are eliminated. An aliquot of each is frozen for later analysis of pepsin. The pH is measured and 1 ml. of gastric juice is titrated with 0.1 N NaOH to a pH of 7.0-7.4. The data are analyzed by an analysis of variance and using the pooled error variance to make t-comparisons between groups.

The use of compounds exhibiting anti-secretory activity in the curative and/or prophylactic treatment of peptic ulcer disease is an established, beneficial procedure.

In addition, the compounds of this invention demonstrate immunomodulatory properties when tested by scientifically recognized procedures in standard experimental animals. Similarly the mesoionic, didehydro form of the compounds of this invention demonstrate immunomodulatory activity. The mesoionic form of the compounds disclosed herein are disproportion products of the corresponding thiazolium salt. Thus, in water, the thiazolium salt is in equilibrium with the mesoionic form and the latter may be simply isolated from the aqueous solution by extraction with a suitable water immiscible solvent such as methylene chloride.

The thiazolium salts of this invention are produced by conventional techniques involving the condensation of an appropriately substituted mercaptan with an α-bromophenylacetic acid, thusly:

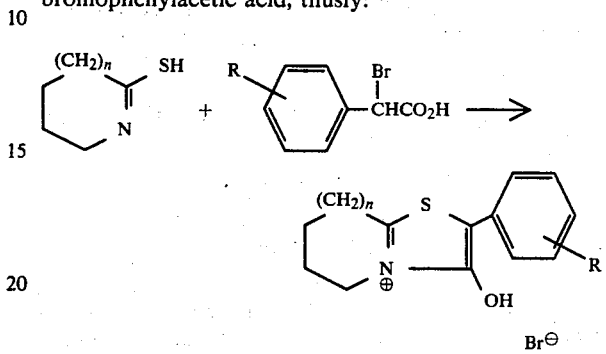

where R is the substituent present upon the R$^1$ phenyl moiety depicted supra. The reactants are either presently available or their preparation is well within the skill of the chemist employing conventional methods of synthesis.

The anti-secretory agents of this invention may be administered orally or parenterally. Liquid compositions include sterile solutions for parenteral administration as well as suspensions, emulsions, syrups and elixirs of the active ingredients for oral administration. The compounds may be employed along as the sole basis for treatment or they may be advantageously employed in conjunction with a treatment regimen utilizing a conventional antacid such as calcium carbonate, magnesium carbonate, bismuth carbonate, aluminum or magnesium hydrated oxides, magnesium glycinate, magnesium trisilicate, calcium trisilicate or sodium bicarbonate to maintain gastric acidity from about a pH of 3 to 5 or higher. Likewise, the anti-secretory agents of this invention may be used in conjunction with anti-cholinergic agents or H$_2$-receptor blocking agents.

Pharmaceutical compositions containing the anti-secretory agents of this invention are formulated conventionally with a solid or liquid carrier. Solid carriers acceptable for use in the administration of anti-secretory agents via tablets, capsules or powders, include magnesium carbonate, magnesium stearate, talc, sugar, lactose, pectin, dextrin, starch, gelatin, tragacanth, methyl cellulose, sodium carboxymethyl cellulose, low melting waxes and cocoa butter. Additional optional ingredients include flavoring agents, lubricants, solubilizers, suspending agents, binders and disintegrants. The quantity of active anti-secretory agent in a solid or liquid composition may be varied widely, such as from about 10 to 80 percent or more.

Unit dosage forms containing from about 10 to 500 milligrams of the compounds are especially suitable for use in oral administration. The dosage regimen for treatment of peptic ulcer disease will depend upon the route of administration, physical condition of the patient and severity of the peptic ulcer disease and must be individualized symptomatically by the attending physician.

The following examples illustrate the preparation of representative compounds of the invention.

EXAMPLE 1

6,7,8,9-Tetrahydro-3-hydroxy-2-phenyl-5H-thiazolo[3,2-a]azepinium bromide

An acetic acid (50 ml.) solution of ω-thiocaprolactam (6.5 g., 0.05 mole) and α-bromophenylacetic acid (10.8 g., 0.05 mole) was heated on a steam bath for ½ hour. The solution was first cooled and diluted with ether. Upon scratching solid which precipitated was collected. The crude material was recrystallized from acetonitrile. The purified material weighed 14 g. (86% yield) and melted at 172°–175° C.

Analysis for: $C_{14}H_{16}BrNOS$. Calculated: C, 51.53; H, 4.94; N, 4.29. Found: C, 51.62; H, 4.93; N, 4.13.

EXAMPLE 2

5,6,7,8-Tetrahydro-3-hydroxy-2-phenylthiazolo[3,2-a]pyridinium bromide

An acetone solution of 3.51 g. (0.03 mole) δ-thiovalerolactam and 6.75 g. (0.03 mole) α-bromophenylacetic acid was heated until the solid started to form. After the solution was cooled, the solid was collected which weighed 6.5 g. Recrystallization could be done with acetonitrile. The purified material had a melting point of 188°–192° (dec.).

Analysis for: $C_{13}H_{14}NOS \cdot Br$. Calculated: C, 50.00; H, 4.52; N, 4.49; S, 10.27. Found: C, 50.26; H, 4.68; N, 4.56; S, 10.38.

EXAMPLE 3

2-(4-Chlorophenyl)-5,6,7,8-tetrahydro-3-hydroxy-thiazolo[3,2-a]-pyridinium bromide A glacial acetic acid solution of 3.45 g. (0.03 mole) of δ-thiovalerolactam and 7.50 g. (0.03 mole) α-bromo-(p-chlorophenyl)acetic acid was heated on a steam bath for 5 hours. After filtration, the solvent was removed. The residual solid upon trituration with acetone was collected. The crude material upon recrystallization from $CH_3CN$ gave 5.6 g. (56% yield). The recrystallized sample had a melting point of 186°–188° C.

Analysis for: $C_{13}H_{13}BrClNOS$. Calculated: C, 45.04; H, 3.78; N, 4.04; Br, 23.05; Cl, 10.23; S, 9.25. Found: C, 45.03; H, 3.71; N, 4.10; Br, 23.30; Cl, 10.33; S, 9.29.

What is claimed is:

1. A compound of the formula:

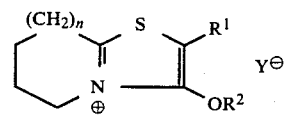

in which

R$^1$ is phenyl, halophenyl, alkylphenyl of 7 to 10 carbon atoms, nitrophenyl or aminophenyl;

R$^2$ is hydrogen or alkanoyl of 2 to 4 carbon atoms;

Y is the anion of a pharmaceutically acceptable acid; and n is one of the integers 1 or 2.

2. The compound of claim 1 which is 6,7,8,9-tetrahydro-3-hydroxy-2-phenyl-5H-thiazolo[3,2-a]azepinium bromide.

3. The compound which is 5,6,7,8-tetrahydro-3-hydroxy-2-phenylthiazolo[3,2-a]pyridinium bromide.

4. The compound of claim 1 which is 2-(4-chlorophenyl)-5,6,7,8-tetrahydro-3-hydroxy-thiazolo[3,2-a]pyridinium bromide.

* * * * *